(12) United States Patent
Perneborn

(10) Patent No.: US 8,267,910 B2
(45) Date of Patent: Sep. 18, 2012

(54) ABSORBING ARTICLE COMPRISING AN ABSORBING STRUCTURE COMPRISING A DEFORMATION LAYER

(75) Inventor: Robert Perneborn, Gothenburg (SE)

(73) Assignee: SCA Hygiene Products AB, Göteborg (SE)

( * ) Notice: Subject to any disclaimer, the term of this patent is extended or adjusted under 35 U.S.C. 154(b) by 0 days.

(21) Appl. No.: 11/576,884

(22) PCT Filed: Nov. 8, 2004

(86) PCT No.: PCT/SE2004/001612
§ 371 (c)(1),
(2), (4) Date: Apr. 8, 2007

(87) PCT Pub. No.: WO2006/049541
PCT Pub. Date: May 11, 2006

(65) Prior Publication Data
US 2008/0065035 A1    Mar. 13, 2008

(51) Int. Cl.
*A61F 13/15* (2006.01)
*A61F 13/20* (2006.01)
(52) U.S. Cl. ............... 604/385.01; 604/367; 604/385.16
(58) Field of Classification Search .......... 604/365–377, 604/385.01, 385.16, 385.24–385.27; 2/365–377, 2/385.01, 385.16, 385.24–385.27
See application file for complete search history.

(56) References Cited

U.S. PATENT DOCUMENTS

| | | | |
|---|---|---|---|
| 4,357,938 A * | 11/1982 | Ito et al. ........................ | 604/376 |
| 4,809,493 A | 3/1989 | Genba et al. | |
| 5,536,264 A * | 7/1996 | Hsueh et al. ................... | 604/368 |
| 5,830,555 A * | 11/1998 | Srinivasan et al. ............ | 428/137 |
| 5,885,264 A | 3/1999 | Matsushita | |
| 5,919,411 A * | 7/1999 | Rezai et al. .................... | 264/154 |
| 5,977,429 A | 11/1999 | Phillips et al. | |
| 6,605,349 B2 | 8/2003 | Phillips | |
| 6,761,709 B2 * | 7/2004 | Morman et al. ........ | 604/385.101 |
| 6,888,046 B2 * | 5/2005 | Toyoshima et al. ........... | 604/380 |
| 6,984,439 B2 * | 1/2006 | Topolkaraev ................. | 428/182 |
| 2003/0044601 A1 | 3/2003 | Phillips | |

FOREIGN PATENT DOCUMENTS

| | | |
|---|---|---|
| EP | 0 661 031 | 11/1994 |
| EP | 0815821 A2 | 1/1998 |
| EP | 0846454 B1 | 11/2000 |

(Continued)

OTHER PUBLICATIONS

Written Opinion from PCT/SE2004/001612 and International Search Report.

(Continued)

*Primary Examiner* — Michele M Kidwell
(74) *Attorney, Agent, or Firm* — Buchanan Ingersoll & Rooney PC

(57) ABSTRACT

An absorbing article, in particular an absorbing structure has at least one layer that can be used with advantage as a surface layer or in combination with a surface layer. The aforementioned layer has deformable fibers which are deformed and shrink when they become wet. The aforementioned layer thus constitutes a deformation layer and has at least one distinct admission passage. The admission passage is deformed and dilated when it becomes wet. In addition to improved admission in conjunction with repeated wetting, the article also offers a solution to the problem of feces handling in combination with repeated wetting.

15 Claims, 4 Drawing Sheets

FOREIGN PATENT DOCUMENTS

| | | |
|---|---|---|
| GB | 2 151 548 | 7/1985 |
| JP | 60-151302 | 8/1985 |
| JP | 7-33916 | 6/1995 |
| JP | 9-28732 | 2/1997 |
| JP | 10-14976 | 1/1998 |
| JP | 11-253490 | 9/1999 |
| JP | 2004-298385 | 10/2004 |
| JP | 2004-298387 | 10/2004 |
| RU | 2 197 212 | 1/2003 |
| WO | WO 98/26741 | 6/1998 |

OTHER PUBLICATIONS

Notice of Reasons for Rejection issued in corresponding Japanese Patent Application No. 2007-540276, mailed Feb. 2, 2010, and English translation thereof.

* cited by examiner

ABSORBING ARTICLE COMPRISING AN ABSORBING STRUCTURE COMPRISING A DEFORMATION LAYER

TECHNICAL FIELD

The invention relates to absorbing articles, preferably diapers, sanitary towels, incontinence guards and panty liners and their absorbing structures. The invention also relates to absorbing structures comprising at least one layer containing deformable fibers which are deformed and shrink when they become wet.

BACKGROUND

Rapid admission has long been a core question in the development of absorbing articles. The rapid admission of liquid into an absorbing article is necessary in order for the liquid to be capable of being dealt with by the absorbing structure. This is especially true in the case of repeated wettings.

In the case of repeated wettings, the storage layers often become saturated locally. This impairs the function of the surface layer and the distribution layers, if any, the purpose of which is rapidly to admit and distribute the liquid. The risk of leakage taking place is increased if admission takes place too slowly. The absorbing article can also become uncomfortable to wear when the surface that faces towards the wearer is wetter for a longer period than normal.

A number of different procedures for improving admission in an absorbing article have been developed over the years. Perforated surface layers, hydrophilic wet areas on the surface layers, distribution layers with a high pore volume (also known as the void volume), to mention only a few. The need remains, however, for further improvements in this area.

There is also a need for solutions which take account of feces handling. Feces handling in absorbing articles and their structures is very often totally neglected when new materials and concepts are being developed. This is in spite of the fact that feces handling remains one of the major unresolved problems in today's diaper industry. Feces handling calls for relatively large open passages in the surface layer to enable the feces to penetrate down into an absorption structure. It is not advantageous, however, for the surface layers to exhibit conspicuous holes. This is because the wearer may draw premature conclusions about the function of the article and its resistance to leakage.

The use of a material that is deformed when it becomes wet is previously disclosed. The expression deformation is used here to denote a change in the structure. A change of this kind may involve the expansion or shrinkage of the material. However, the material must preferably not undergo any chemical change. The deformation is more often than not initiated by a special factor, for example temperature, pH or in the event of contact with liquid. A layer which meets these criteria can be termed a deformation layer.

Described in U.S. Pat. No. 5,885,264 is an absorbing article with a layer positioned on the surface layer, which shrinks when it becomes wet. The purpose of this layer is to indicate that the wearer has wet the diaper, and to ensure that the wearer experiences a sensation of wetness against the skin. When the wearer is an infant, a product of this kind can be used, for example, for potty training.

Described in EP 846,454 A1 is a backing layer which shrinks when it is exposed to liquid. The material that is used to impart the shrinking property contains polymers such as polyvinyl alcohol with a degree of hydrolysis of at least 88%, preferably 95%, and if at all possible at least 98%. The polyvinyl alcohol is produced by the hydrolysis of polyvinyl acetate. The expression degree of hydrolysis is used here to denote the percentage expressed in mol by which the acetate groups have been replaced with hydroxyl groups. The higher the degree of hydrolysis of the polyvinyl alcohol, the higher is the crystalline nature of the polyvinyl alcohol. This is explained in EP 846,454 A1 by the fact that the crystallinity of the polyvinyl alcohol is in direct proportion to the ability of the polymer to shrink when it comes into contact with liquid. A high crystallinity thus gives greater shrinkage, i.e. the material shrinks more.

The crystallinity can also be improved, and with it the polymer's property of being able to shrink, by increasing the degree of replaced acetate groups by purely chemical means. The crystallinity can also be improved by processing the polymer by adequate mechanical stretching. This is customarily achieved, for example, during the formation of fibers and structures such as layers and films.

When polyvinyl alcohol shrinks, this is attributable to the partial decomposition and/or plasticization of the crystalline structure of the polyvinyl alcohol through contact with the liquid. This takes place at a molecular level. Due to the fact that the crystalline structure was formed during stretching, any residual unbalanced stress remains in the material. The crystals are plasticized on contact with liquid and become softer. As a result of this, the internal stresses in the material become lower and permit the material to resume its earlier structure.

Described in U.S. Pat. No. 6,605,349 B2 is a deformable shrink fiber. The dimensions of the fiber are said to be stable at normal body temperature (ca 37° C.) in its dry state. The dimensions are unstable, however, in the wet state at the same temperature, i.e. the fiber shrinks and is deformed. The fiber contains a fiber-shaped polymer that has a dry glass transition temperature ("dry Tg") greater than or equal to 42° C., and a wet glass transition temperature ("wet Tg") less than or equal to 32° C.

Further examples of shrink fibers are described in U.S. Pat. No. 4,357,938, where shrink fibers are laid in a longitudinal direction alongside the absorption body in order to cause it to flex when it becomes wet.

Room is accordingly available for a solution which improves the currently available absorbing structures and absorbing articles, on the one hand a solution which permits more rapid admission in conjunction with repeated wetting, and on the other hand a solution which can provide feces with the possibility of penetrating down into the absorbing structure and, in so doing, avoid irritation to a wearer's skin.

SUMMARY

An absorbing structure and absorbing articles are disclosed which essentially avoid the problems associated with previously disclosed structures and articles of this kind. An absorbing structure is characterized first and foremost in that it comprises a deformation layer and at least one distinct admission passage, which admission passage is deformed and dilated when it becomes wet.

The expression distinct admission passage is used here and below to denote a specific passage, via which liquid shall be capable of passing through a layer in conjunction with wetting of the absorbing article and its absorption structure. The expression distinct admission passage does not denote the cavities between the fibers which may be formed naturally, for example in an airlaid cellulose fluff body or in a nonwoven surface layer. Natural cavities can be referred to as an admission passage, but not as a distinct admission passage. A surface layer that is perforated with holes exhibits distinct admission passages. The holes in this case are produced for the specific purpose of facilitating penetration by the liquid into the absorbing structure. The expression admission denotes that both feces and liquid can penetrate into the absorption structure.

The disclosed structure is positioned preferably in that part of the absorbing article which, when it is being worn, is envisaged to face towards the wearer. The structure is thus able to function as part of a surface layer or a liquid distribution layer. Alternatively, it can function as a volume-creating surface layer. When the admission passages are deformed in conjunction with wetting, this gives a more open structure and better admission in conjunction with rewetting.

The deformation layer can be attached to a carrier layer, for example by means of adhesive, ultrasonic welding or a similar means of attachment. The carrier layer may consist of, for example, a tissue layer, a perforated film, a mesh or a nonwoven layer, for example made of polypropylene or polyethylene or mixtures thereof. The purpose of the carrier layer is to facilitate manufacture and attachment to any additional absorption layer.

The function of the carrier layer is especially clear when at least two deformation layers are positioned essentially parallel to one another in the horizontal plane on a carrier layer. Distinct liquid passages are then formed between the two deformation layers. It falls within the scope of the invention that a distinct admission passage may exhibit a width of 0 mm before wetting, only to open up after wetting. The expression 0 mm is used here to denote that the sides of the admission passage are in contact with one another before wetting. The preferred width between the deformation layers may be 0-10 mm, and preferably 0-3 mm.

In certain embodiments, as many as six deformation layers may lie essentially parallel to one another. It is nevertheless within the scope of the invention for at least 2, 3, 4, 5, 6, 7, 8, 9 or 10 deformation layers to lie essentially parallel to one another. The expression essentially parallel is used to denote that they shall lie as parallel to one another as it is reasonably possible to achieve in production and, unless stipulated to the contrary, parallel in the horizontal plane. It must be pointed out that there is always a certain variation and margin of error in production, which may be considered to be included in the concept of essentially. The deformation layers do not need to lie parallel in certain embodiments. They may lie at an angle to one another or in irregular or regular patterns, such as a number of circular formations, oval formations, rectangular formations, triangular formations and the like. The pattern of the deformation layers is adapted according to need.

The deformation layer may also comprise a so-called supporting layer. The function of the supporting layer in one embodiment is to form the distinct admission passages in conjunction with wetting, for example as shown in FIGS. 3a and 3c. The supporting layer is not intended to be made from a material that shrinks in conjunction with wetting. A curved form is accordingly obtained in conjunction with wetting. The curved form may be said to resemble the letter J. If the deformation layer is positioned beneath a surface layer, above an absorption layer, for example in a diaper, the curved form may be utilized in order to obtain volume between the surface layer and the absorption layer. This volume can give the wearer a sensation that the surface layer is dry when the surface layer is not in contact with the liquid that is being stored in the absorption layer.

If the deformation layer consists of a layer that is itself homogeneous, the distinct admission passages can be made of slotted holes. The slots are produced, for example, with a "rotary die cut" (RDC) roller. The slots can be 5-50 mm long before wetting. The width in conjunction with slotting is ca 0-3 mm. The expression 0 mm is used here to denote that a slot has been made. The fibers in the cut surfaces may engage with one another after slotting, however. This means that a distinct admission passage may, at first sight, appear to be 0 mm, in spite of the fact that the cut surfaces are present at that point. The distinct admission passage becomes clear, however, in conjunction with wetting. The distinct admission passages can also be punched out using tools familiar in this field. The length in this case is also 5-50 mm, and the width of the distinct admission passage is 2-10 mm.

The absorbing structure can in turn be positioned with advantage in combination with additional absorption layers such as storage layers or the like. The structure is then preferably positioned on the side of the absorption layer that faces towards the wearer during use. The absorption layer may consist of a number of different materials that are already familiar in the field, such as superabsorbings, odor inhibitors and the like. The absorption layer can also consist of a number of different absorption layers, layers of cellulose material, layers of superabsorbings, layers of odor inhibitors and the like.

The absorbing structure can be enclosed by a layer of tissue or some other layer to facilitate handling and to give increased comfort. A further surface layer can, for example, render the deformation layer invisible to the daily wearer or provide a softer surface towards the wearer.

The invention can be positioned with advantage in an absorbing article, and preferably in a diaper, incontinence guard or panty liner.

BRIEF DESCRIPTION OF THE FIGURES

The embodiments of the invention are described below in greater detail with reference to the following Figures, where.

DESCRIPTION OF EMBODIMENTS

The invention relates to an absorbing article, such as a diaper, an incontinence guard or the like. More specifically, the invention relates to a surface layer, part of a surface layer, a distribution layer or part of a distribution layer. An object of the invention is, among other things, to permit increased admission into the absorbing article on conjunction with repeated wetting.

Figure 1:
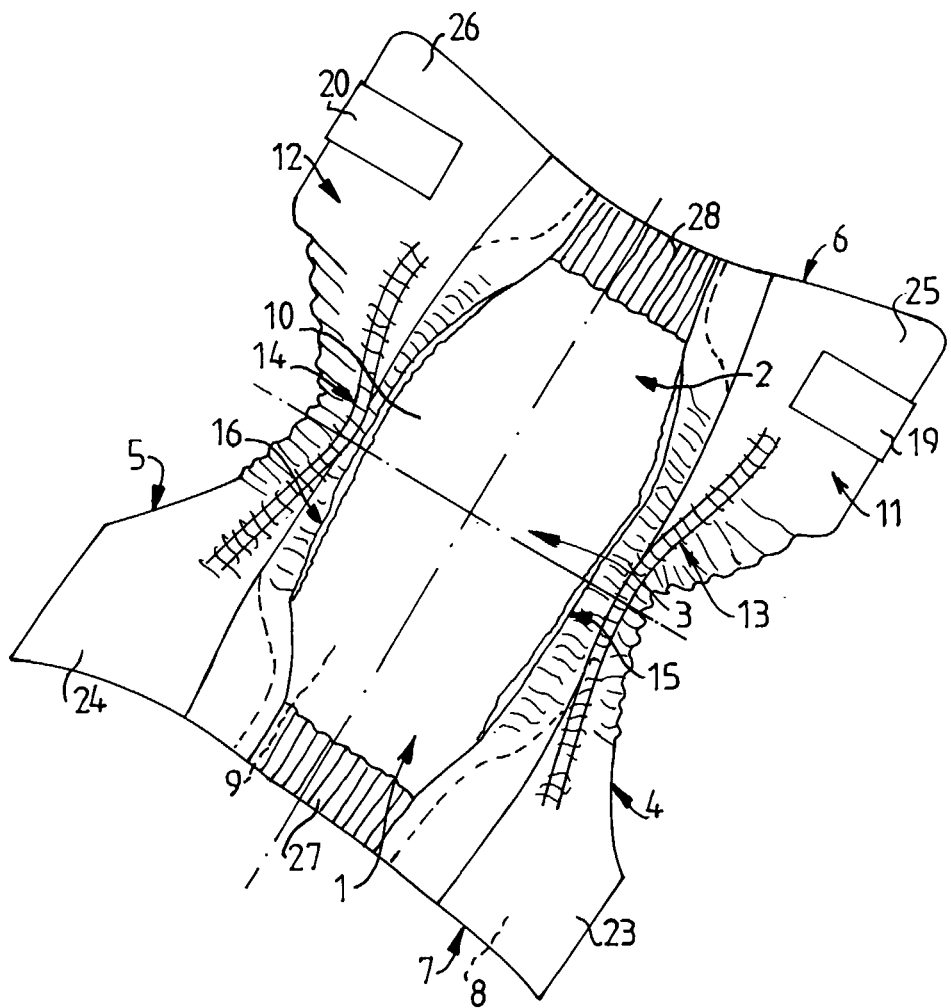
FIG. 1 shows a diaper viewed towards the surface layer.

A diaper will be described primarily as an example of an absorbing article. The diaper has a longitudinal center line and a transverse center line. Illustrated in FIG. 1 is a diaper comprising a front and a rear end part 1,2, an interjacent crotch part 3 which, when the diaper is being worn, is intended to be applied between a wearer's legs, longitudinal side edges 4,5 and transverse side edges 6,7, a lower, liquid-tight backing layer 8, an absorption structure 9, a first liquid-permeable surface layer 10, and longitudinal leakage barriers 15,16. The leakage barriers 15,16 contain elastic and are accordingly gathered together at least in their central part. Side flaps 11,12, which extend laterally outside the leakage barriers 15,16 and at least in the crotch part 3, exhibit longitudinal elastic elements 13,14 along their free side edges, which elastic elements 13,14 serve as leg elastic while the article is being worn.

The diaper also includes attachment arrangements 19,20 (here shown folded in towards the surface layer of the diaper) in the form of Velcro®, although tape with adhesive can also be used.

Figure 2:
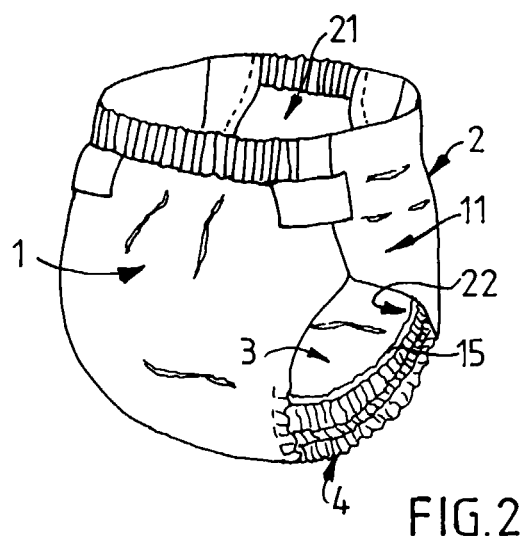
FIG. 2 shows a diaper arranged as in normal use.

The front 23,24 and rear 25,26 ends of the side flaps 11,12 can be seen on the front end part 1 and the rear end part 2 of the diaper. The absorbing article in FIGS. 1 and 2 exhibits front and rear waist elastic 27,28 respectively between the front 23,24 and rear 25,26 ends of the side flaps 11,12. As shown in FIGS. 1 and 2, these can be present on the transverse edges 6,7. The front and rear waist elastic 27,28 extends for approximately one third of the length of the transverse edges 6,7. In other embodiments, only a rear waist elastic may be present. Waist elastic may also be present which extends over both of the transverse edges of the entire absorbing article.

The appearance of the diaper when it is being worn is illustrated in FIG. 2. The front end part 1 and the rear end part 2 of the diaper, together with the interjacent crotch part 3, can be seen here. The front part 1 is attached to the rear part 2 by means of the attachment arrangements 19,20, and an opening 21 for the wearer's abdomen is formed at the top of the diaper, and an opening 22 for the wearer's legs is also visible. A side flap 11 and an upward-projecting leakage barrier 15 can be seen at the edge of the opening for the wearer's legs 22, which is bounded by a side edge 4 on the article. The leakage barrier 15 is gathered, at least in its centermost part, by means of elastic elements that are attached in a pre-tensioned state to the leakage barrier 15. The elastic is tensioned during use, which means that the leakage barrier 15 faces upwards towards the wearer and fits closely round the wearer's legs so that leakage is prevented.

The absorption structure 9 can consist of cellulose fluff with or without the admixture of so-called super-absorbing articles. However, the absorption body can be constructed from any standard material or materials used in absorption bodies for absorbing articles such as diapers, pant diapers, incontinence guards, panty liners or the like. The absorption structure 9 can also be constructed from more than one layer of absorbing material. Absorbing structures usually contain layers of wadding, so-called distribution layers, to enable the rapid removal of excreted liquid from the liquid-receiving surface layer 10. Each of the layers comprised in the absorption structure 9 can, of course, contain superabsorbings. A number of absorbing structures of a kind that could fit in the absorbing article are described in greater detail in EP 659, 541. Other examples of absorbing structures can be found in WO 93/21882, for example. The invention is not restricted to these embodiments alone, however, and they must only be regarded as examples.

The liquid-tight backing layer 8 can consist of or can comprise a liquid-tight plastic film, a nonwoven layer that has been coated with a liquid-blocking material, or some other pliable layer of material with the ability to resist penetration by liquid. It is generally an advantage if the liquid-tight backing layer 8 exhibits breathability, that is to say permits the passage of water vapor through the layer 8.

Illustrated in FIGS. 3a-3d is a carrier layer 301, which exhibits six longitudinal deformation layers 302 in the direction of the machine. The carrier layer 301 in FIGS. 3a-3d is intended to face away from the wearer when wearing the diaper, and the deformation layer 302 is intended to face towards the wearer when wearing the diaper. The deformation layer 302 is securely arranged on the carrier layer 301 by means of a string of adhesive 303. The string of adhesive 303 in FIGS. 3a-3d is positioned to the right-hand side of the deformation layer 302. It is, of course, possible to use methods of attachment other than adhesive. For example, ultrasonic welding can be used. The method of attachment can be in the form of individual points, continuous lines, broken lines, sinusoidal lines or oblique lines. For the sake of clarity, a row with a number of points may be regarded here as constituting a line. It also lies within the scope of the invention, for example, for a string of adhesive to be placed in the center of the deformation layer or on the left-hand side of the deformation layer (FIGS. 4a-4b).

A distinct admission passage 306 can be seen between each deformation layer 302 in FIGS. 3a-3d. The expression distinct admission passage denotes a specific passage through which liquid must be capable of passing in conjunction with wetting of the absorbing article and its absorption structure 9. The expression distinct admission passage does not denote the cavities between the fibers that can be formed naturally, for example in a cellulose fluff pulp body. The distinct admission passage has been created, for example, by cutting into the deformation layer 302, or, as shown in FIGS. 3a-3d, by a predetermined space between a number of deformation layers.

The deformation layer 302 in FIGS. 3a-3d exhibits two layers. On the side that is intended to face towards the wearer when wearing the diaper, a layer of deformable fibers 304 is present, which fibers, in conjunction with wetting, are caused to deform and shrink. Such fibers have previously been described and will not be discussed in any greater detail here, although fibers of polyvinyl alcohol can be mentioned by way of example. Positioned on the side of the deformable fiber layer 304 facing away from the user is a layer of nonwoven fiber, for example polypropylene fiber, referred to below as the supporting layer 305.

The deformable fiber layers 304 are positioned on the supporting layer 305 and are jointly referred to as the deformation layer 302. The deformation layer 302 is securely arranged on the carrier layer 301.

Figure 3A:
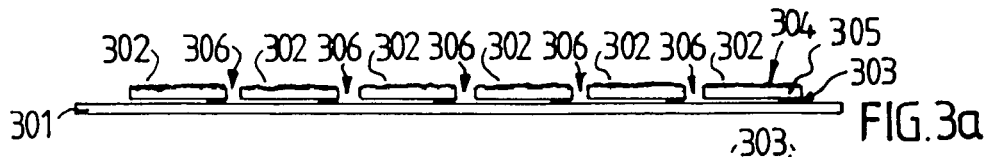
FIG. 3a shows a number of deformation layers in the dry state positioned on a carrier layer viewed in cross section.
Figure 3B:
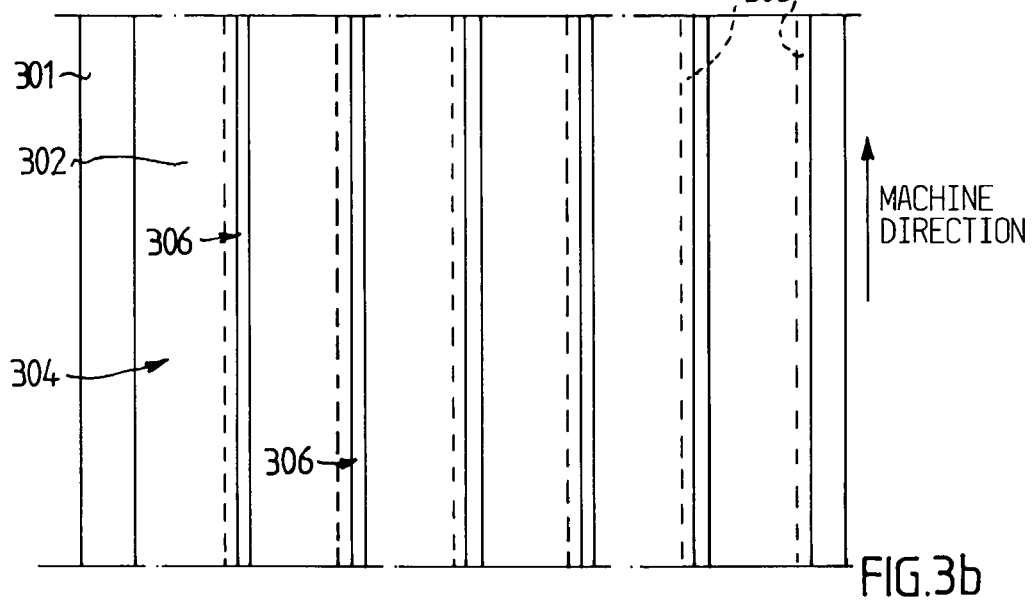
FIG. 3b shows a number of deformation layers in the dry state positioned on a carrier layer viewed perpendicular to the surface from above.
Figure 3C:
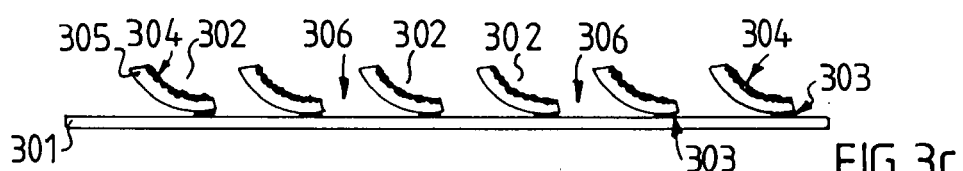
FIG. 3c shows a number of deformation layers in the wet state positioned on a carrier layer viewed in cross section.
Figure 3D:
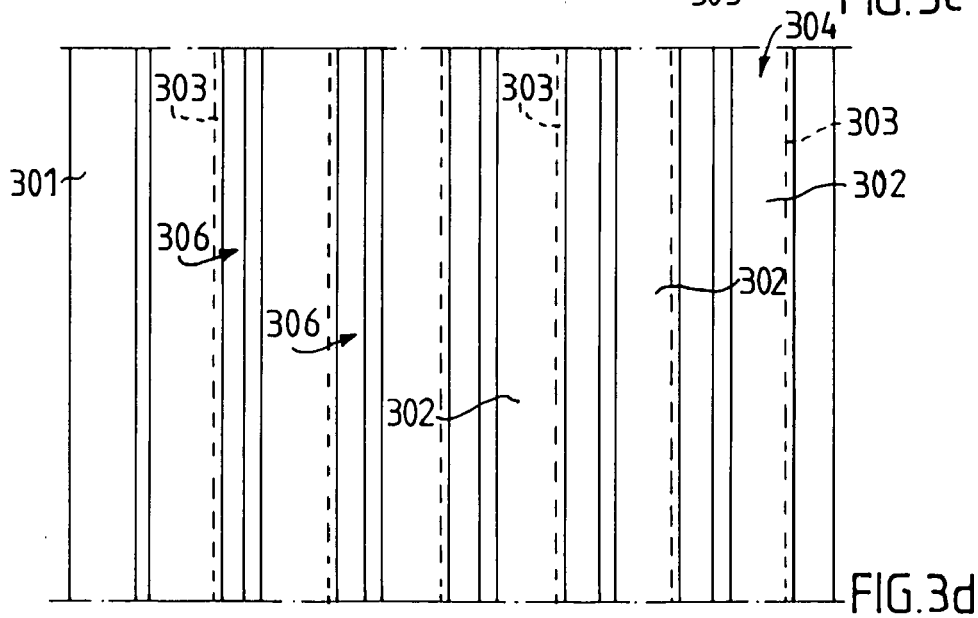
FIG. 3d shows a number of deformation layers in the wet state positioned on a carrier layer viewed from above.
Figure 4A:
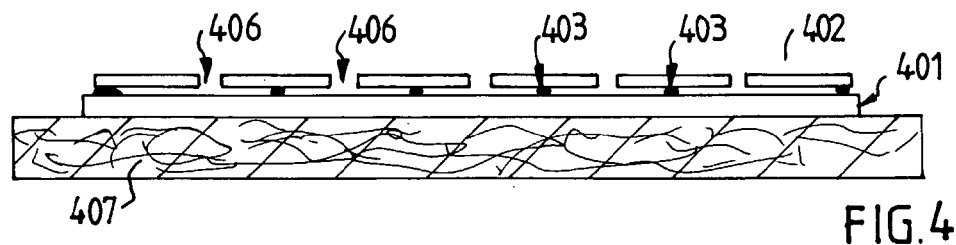
FIGS. 4a-4b show a deformation layer with a carrier layer positioned on an absorption body viewed in cross section.
Figure 4B:
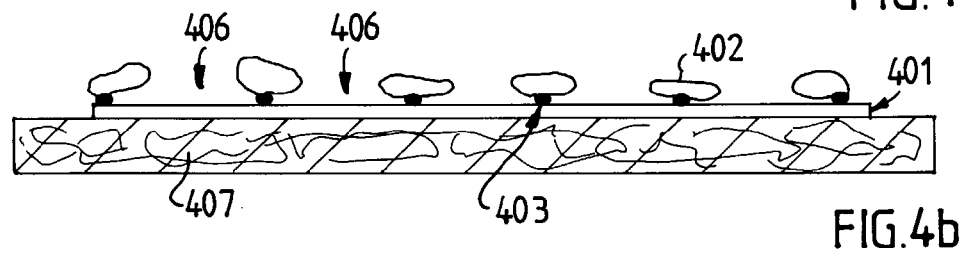

The carrier layer 301 with the deformation layer 302 can be seen in cross section in FIG. 3a. The same layer is shown from above in FIG. 3b. The layers are shown in the dry state in FIGS. 3a and 3b before any deformation has taken place. In FIGS. 3c-3d, the layers have been subjected to wetting, for example urine from a wearer. The deformable fiber layers 304 have been deformed and have shrunk in conjunction with this. The deformation layer 302 flexes in such a way that the distinct admission passage 306 is dilated and can permit more rapid admission into the absorbing structure and the absorbing article.

An absorbing structure viewed in cross section is shown in FIGS. 4a-4b. The deformation layers 402 are securely arranged on a carrier layer 401 by ultrasonic welding. The deformation layers 402 here consist of only a single layer. This layer can consist either entirely of deformable fibers which shrink in conjunction with wetting, or of a mixture of deformable fibers which shrink and ordinary synthetic fibers, for example polypropylene fibers or polyethylene fibers. A combination with cellulose fibers is also possible.

The ultrasonic welds 403 can be positioned at different points so that they secure the deformation layers 402 differently. This offers a number of advantages for the absorbing structure. For example, the deformation layers can be deformed and can shrink so that the resulting different distinct admission passages are of different sizes.

The deformation layers 402 are positioned parallel to one another in their horizontal extent, so that distinct admission passages 406 are formed between the deformation layers. The distinct admission passages have been dilated in FIG. 4b after having been subjected to wetting, and the deformation layers 402 have contracted. This means that, in conjunction with repeated wetting, the deformation layer exhibits a higher admission rate, and in certain cases a significantly higher admission rate.

An absorption layer 407 is positioned under the carrier layer 401 and, as previously described, this absorption layer can comprise one or more layers.

A number of absorbing structures, which would be able to be utilized in combination with the invention, are described in greater detail in EP 659,541. Other suitable examples of absorbing structures can be found in WO 93/21882, for example. The invention is not restricted to these alone, however, and they must only be regarded as examples.

Figure 5A:
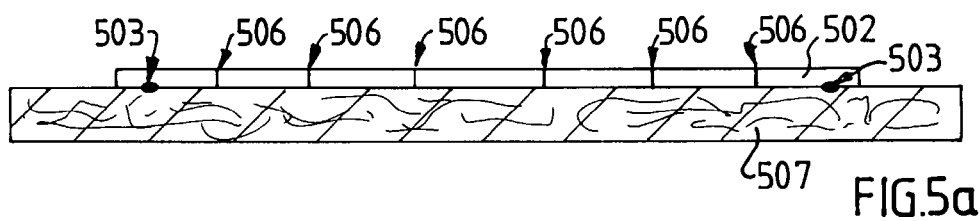
FIG. 5a shows a deformation layer positioned on an absorption layer viewed in cross section.
Figure 5B:
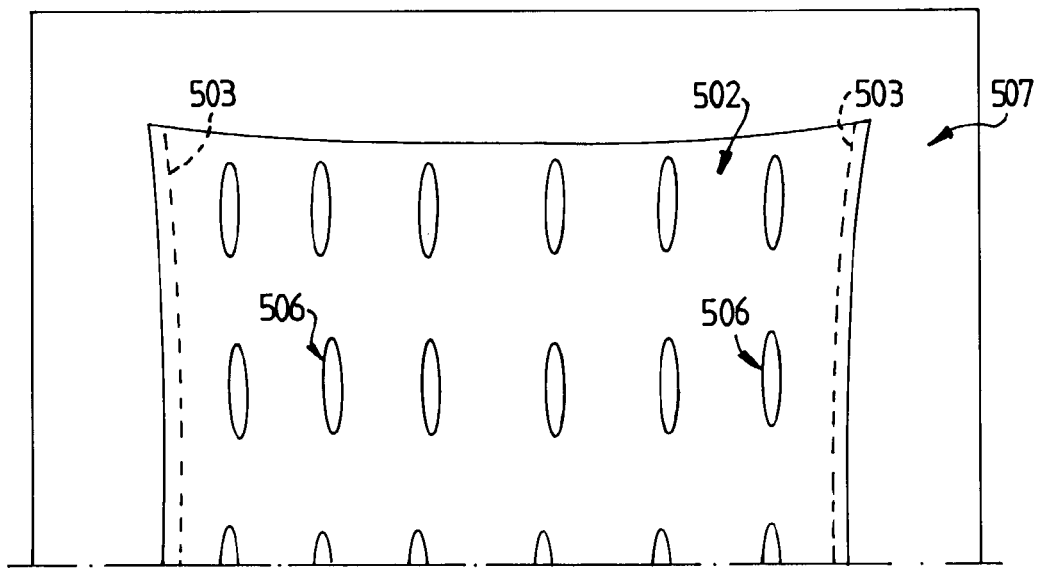
FIG. 5b shows a deformation layer positioned on an absorption layer viewed from above.

A further illustrative embodiment of the invention is shown in FIGS. 5a-5b. In this illustrative embodiment, only a single deformation layer 502 is positioned on an absorption layer 507. The deformation layer 502 is attached to the absorption layer 507 by means of two strings of adhesive 503. It lies within the scope of the invention, of course, for a number of other methods of attachment to be used.

The deformation layers 502 exhibit a number of distinct admission passages 506. The distinct admission passages have been cut with a so-called "rotary die cut" (RDC) roller. There are of course different ways of creating distinct admission passages in a layer. Punching holes is another way. The absorption structure illustrated in FIG. 5a is seen in cross section before wetting. The distinct admission passages can be seen only as small cuts through the entire deformation layer 502. The absorption structure is shown after wetting in FIG. 5b. The distinct admission passages have been dilated by the deformation and shrinkage of the deformable fibers in the deformation layer 502. The deformation layer 502 in this case has contracted. The dilation of the distinct admissions passages 506 permits the admission to be accelerated in conjunction with the next wetting, because the liquid is then able to gain more rapid access to the subjacent absorption body.

Figure 6A:
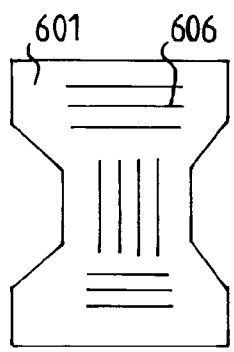
FIGS. 6a-6f show illustrative embodiments of the configuration of distinct admission passages.
Figure 6B:
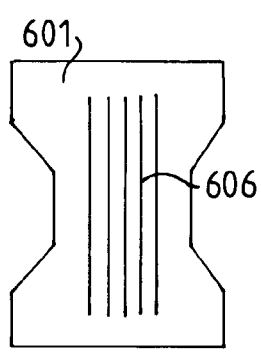
Figure 6C:
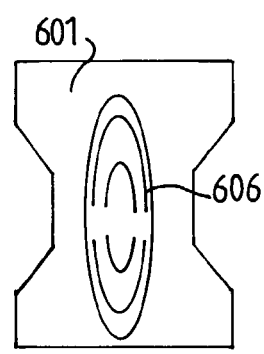
Figure 6D:
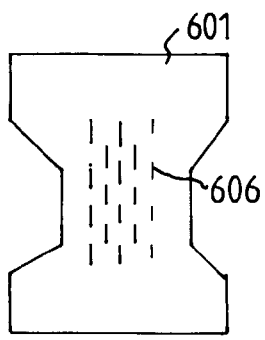
Figure 6E:
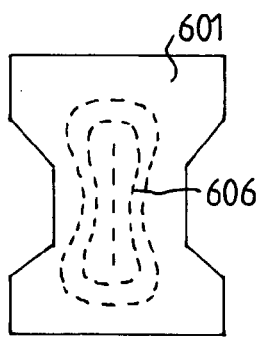
Figure 6F:
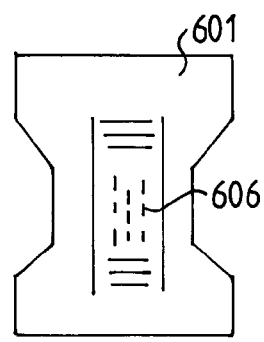

Schematic images of absorbing articles are shown in FIGS. 6a-6c. Patterns of distinct admission passages 606 can be seen in the figures. For the sake of clarity, the other components that a diaper may contain are not shown in the schematic figures. Combinations of the embodiments of the invention illustrated in FIGS. 3-5 naturally lie within the scope of the invention. Any such combinations can also be positioned in accordance with the schematic FIGS. 6a-6f.

LIST OF REFERENCE DESIGNATIONS

1 Front end part
2 Rear end part
3 Interjacent crotch part
4 Longitudinal side edge
5 Longitudinal side edge
6 Transverse side edge
7 Transverse side edge
8 Liquid-tight backing layer
9 Absorption structure
10 Liquid-permeable surface layer
11 Side flaps
12 Side flaps
13 Elastic elements
14 Elastic elements
15 Longitudinal leakage barriers
16 Longitudinal leakage barriers
19 Attachment arrangements
20 Attachment arrangements
21 Opening for wearer's abdomen
22 Opening for wearer's legs
23 Front ends of side flaps 11,12
24 Front ends of side flaps 11,12
25 Rear ends of side flaps 11,12
26 Rear ends of side flaps 11,12
27 Front waist elastic
28 Rear waist elastic
301 Carrier layer
302 Deformation layer
303 String of adhesive
304 Deformable fiber layer
305 Supporting layer
306 Distinct admission passage
401 Carrier layer
402 Deformation layer
403 Ultrasonic welds
406 Distinct admission passage
407 Absorption layer
502 Deformation layer
503 String of adhesive
506 Distinct admission passage
507 Absorption layer
601 Schematic images of absorbing article
606 Pattern of distinct admission passages

The invention claimed is:

1. An absorbing structure comprising
   at least one deformation layer, which layer comprises deformable fibers which are deformed and shrink when they become wet,
   the deformation layer comprises at least one distinct admission passage, which admission passage is deformed and dilated when the deformation layer becomes wet,
   the at least one distinct admission passage constitutes a spacing other than a naturally formed cavity between fibers.

2. The absorbing structure as claimed in claim 1, further comprising a carrier layer, and the deformation layer is attached to the carrier layer.

3. An absorbing structure comprising
   at least one deformation layer, which layer comprises deformable fibers which are deformed and shrink when they become wet,
   a carrier layer, and the deformation layer is attached to the carrier layer,
   wherein the absorbing structure has at least two deformation layers positioned essentially parallel to one another on the carrier layer, and
   a distinct admission passage is formed between the two deformation layers, which admission passage is deformed and dilated when the deformation layer becomes wet.

4. The absorbing structure as claimed in claim 2, wherein the absorbing structure has at least six deformation layers positioned essentially parallel to one another on the carrier layer.

5. The absorbing structure as claimed in claim 2, wherein the deformation layer includes a supporting layer.

6. The absorbing structure as claimed in claim 1, wherein the at least one distinct admission passage comprises slotted holes in the deformation layer.

7. The absorbing structure as claimed in claim 1, wherein a length of the at least one distinct admission passage, which comprises slotted holes in the deformation layer, is about 5-50 mm before wetting.

8. The absorbing structure as claimed in claim 1, wherein the at least one distinct admission passage comprises the space that is obtained when at least two deformation layers have been positioned essentially parallel to one another.

9. The absorbing structure as claimed in claim 8, wherein the distance between the two deformation layers before wetting is 0-3 mm.

10. The absorbing structure as claimed in claim 1, wherein the absorbing structure further comprises an absorption layer as a storage layer.

11. The absorbing structure as claimed in claim 1, wherein the absorbing structure is enclosed by a tissue layer.

12. An absorbing article comprising an absorbing structure as claimed in claim 1.

13. The absorbing article comprising an absorbing structure as claimed in claim 12, wherein the absorbing article is a diaper, sanitary towel, incontinence product or panty liner.

14. An absorbing structure comprising:
at least one deformation layer, which layer comprises deformable fibers which are deformed and shrink when they become wet,
the deformation layer comprises at least one distinct admission passage, which admission passage is deformed and dilated when the deformation layer becomes wet,
wherein the at least one distinct admission passage constitutes one of:
a spacing between adjacent portions of the deformation layer, and
a spacing created by cutting into the deformation layer.

15. The absorbing structure of claim 1, wherein there are a plurality of distinct admission passages, wherein at least two of the plurality of distinct admission passages are of a substantially different size from each other.

* * * * *